(12) United States Patent
Rossetto et al.

(10) Patent No.: US 7,998,139 B2
(45) Date of Patent: Aug. 16, 2011

(54) COOLED HELICAL ANTENNA FOR MICROWAVE ABLATION

(75) Inventors: Francesca Rossetto, Longmont, CO (US); Mani N. Prakash, Boulder, CO (US); Jolie Masangcay, Mountain House, CA (US)

(73) Assignee: Vivant Medical, Inc., Boulder, CO (US)

( * ) Notice: Subject to any disclaimer, the term of this patent is extended or adjusted under 35 U.S.C. 154(b) by 1147 days.

(21) Appl. No.: 11/789,521

(22) Filed: Apr. 25, 2007

(65) Prior Publication Data

US 2008/0266203 A1     Oct. 30, 2008

(51) Int. Cl.
    A61B 18/18      (2006.01)
(52) U.S. Cl. .......................................... 606/33; 607/156
(58) Field of Classification Search ............... 606/33; 607/156
    See application file for complete search history.

(56) References Cited

U.S. PATENT DOCUMENTS

| | | |
|---|---|---|
| 4,140,130 A | 2/1979 | Storm, III |
| 4,311,154 A | 1/1982 | Sterzer et al. |
| D263,020 S | 2/1982 | Rau, III |
| 4,409,993 A | 10/1983 | Furihata |
| 4,534,347 A | 8/1985 | Taylor |
| 4,557,272 A | 12/1985 | Carr |
| 4,583,869 A | 4/1986 | Chive et al. |
| 4,612,940 A | 9/1986 | Kasevich et al. |
| 4,621,642 A | 11/1986 | Chen |
| 4,632,128 A | 12/1986 | Paglione et al. |
| 4,658,836 A | 4/1987 | Turner |
| 4,700,716 A | 10/1987 | Kasevich et al. |
| D295,893 S | 5/1988 | Sharkany et al. |
| D295,894 S | 5/1988 | Sharkany et al. |
| 4,776,086 A | 10/1988 | Kasevich et al. |
| 4,800,899 A | 1/1989 | Elliott |
| 4,823,812 A | 4/1989 | Eshel et al. |
| 4,825,880 A | 5/1989 | Stauffer et al. |
| 4,841,988 A | 6/1989 | Fetter et al. |
| 4,945,912 A | 8/1990 | Langberg |
| 5,057,106 A * | 10/1991 | Kasevich et al. ............... 606/33 |
| 5,097,845 A | 3/1992 | Fetter et al. |
| 5,122,137 A | 6/1992 | Lennox |
| 5,190,054 A | 3/1993 | Fetter et al. |
| 5,220,927 A | 6/1993 | Astrahan et al. |
| 5,221,269 A | 6/1993 | Miller et al. |
| 5,234,004 A | 8/1993 | Hascoet et al. |
| 5,246,438 A | 9/1993 | Langberg |

(Continued)

FOREIGN PATENT DOCUMENTS

CN       1103807       6/1995

(Continued)

OTHER PUBLICATIONS

International European Search Report EP 08007924 dated Aug. 17, 2010.

(Continued)

*Primary Examiner* — Lee S Cohen

(57) ABSTRACT

A microwave antenna assembly including an elongated cooling jacket having proximal and distal ends and an inner lumen defined therebetween and a helical microwave antenna member disposed within at least a portion of the elongated cooling jacket and having an inner and outer conductor, the inner conductor disposed within the outer conductor, wherein at least a portion of the inner conductor extends distally from the outer conductor and forms at least one loop; and wherein the inner conductor is configured to deliver microwave energy.

17 Claims, 9 Drawing Sheets

U.S. PATENT DOCUMENTS

| | | | |
|---|---|---|---|
| 5,249,585 A | 10/1993 | Turner et al. | |
| 5,275,597 A | 1/1994 | Higgins et al. | |
| 5,281,217 A | 1/1994 | Edwards et al. | |
| 5,301,687 A | 4/1994 | Wong et al. | |
| 5,314,466 A | 5/1994 | Stern et al. | |
| 5,342,355 A | 8/1994 | Long | |
| 5,344,435 A | 9/1994 | Turner et al. | |
| 5,344,441 A | 9/1994 | Gronauer | |
| 5,366,490 A | 11/1994 | Edwards et al. | |
| 5,370,644 A | 12/1994 | Langberg | |
| 5,383,922 A | 1/1995 | Zipes et al. | |
| 5,405,346 A | 4/1995 | Grundy et al. | |
| 5,413,588 A | 5/1995 | Rudie et al. | |
| 5,458,597 A | 10/1995 | Edwards et al. | |
| 5,464,445 A | 11/1995 | Rudie et al. | |
| 5,480,417 A | 1/1996 | Hascoet et al. | |
| 5,500,012 A | 3/1996 | Brucker | |
| 5,507,743 A | 4/1996 | Edwards et al. | |
| 5,509,929 A | 4/1996 | Hascoet et al. | |
| 5,520,684 A | 5/1996 | Imran | |
| 5,536,267 A | 7/1996 | Edwards et al. | |
| 5,545,137 A | 8/1996 | Rudie et al. | |
| 5,556,377 A | 9/1996 | Rosen et al. | |
| 5,599,294 A | 2/1997 | Edwards et al. | |
| 5,599,295 A | 2/1997 | Rosen et al. | |
| 5,620,480 A | 4/1997 | Rudie | |
| 5,628,770 A | 5/1997 | Thome et al. | |
| 5,683,382 A * | 11/1997 | Lenihan et al. | 606/33 |
| 5,720,718 A | 2/1998 | Rosen et al. | |
| 5,741,249 A | 4/1998 | Moss et al. | |
| 5,755,754 A | 5/1998 | Rudie et al. | |
| 5,776,176 A | 7/1998 | Rudie | |
| 5,800,486 A | 9/1998 | Thome et al. | |
| 5,800,494 A * | 9/1998 | Campbell et al. | 607/116 |
| 5,810,803 A | 9/1998 | Moss et al. | |
| 5,810,804 A | 9/1998 | Gough et al. | |
| 5,829,519 A | 11/1998 | Uthe | |
| 5,843,144 A | 12/1998 | Rudie et al. | |
| 5,871,523 A | 2/1999 | Fleischman et al. | |
| 5,897,554 A | 4/1999 | Chia et al. | |
| 5,902,251 A * | 5/1999 | vanHooydonk | 600/549 |
| 5,904,691 A | 5/1999 | Barnett et al. | |
| 5,904,709 A | 5/1999 | Arndt et al. | |
| 5,916,240 A | 6/1999 | Rudie et al. | |
| 5,931,807 A | 8/1999 | McClure et al. | |
| 5,938,692 A | 8/1999 | Rudie | |
| 5,951,547 A | 9/1999 | Gough et al. | |
| 5,957,969 A * | 9/1999 | Warner et al. | 607/156 |
| 5,964,755 A | 10/1999 | Edwards | |
| 5,974,343 A | 10/1999 | Brevard et al. | |
| 5,980,563 A | 11/1999 | Tu et al. | |
| 5,997,532 A | 12/1999 | McLaughlin et al. | |
| 6,016,811 A | 1/2000 | Knopp et al. | |
| 6,026,331 A | 2/2000 | Feldberg et al. | |
| 6,032,078 A | 2/2000 | Rudie | |
| 6,047,216 A | 4/2000 | Carl et al. | |
| D424,694 S | 5/2000 | Tetzlaff et al. | |
| D425,201 S | 5/2000 | Tetzlaff et al. | |
| 6,056,744 A | 5/2000 | Edwards | |
| 6,059,780 A | 5/2000 | Gough et al. | |
| 6,063,078 A | 5/2000 | Wittkampf | |
| 6,073,051 A | 6/2000 | Sharkey et al. | |
| 6,080,150 A | 6/2000 | Gough et al. | |
| 6,097,985 A * | 8/2000 | Kasevich et al. | 607/102 |
| 6,106,518 A | 8/2000 | Wittenberger et al. | |
| 6,122,551 A | 9/2000 | Rudie et al. | |
| 6,134,476 A | 10/2000 | Arndt et al. | |
| 6,146,379 A | 11/2000 | Fleischman et al. | |
| 6,176,856 B1 | 1/2001 | Jandak et al. | |
| 6,181,970 B1 | 1/2001 | Kasevich | |
| 6,217,528 B1 | 4/2001 | Koblish et al. | |
| 6,223,086 B1 | 4/2001 | Carl et al. | |
| 6,226,553 B1 | 5/2001 | Carl et al. | |
| 6,233,490 B1 | 5/2001 | Kasevich | |
| 6,235,048 B1 | 5/2001 | Dobak, III | |
| 6,245,064 B1 | 6/2001 | Lesh et al. | |
| 6,251,128 B1 | 6/2001 | Knopp et al. | |
| 6,275,738 B1 | 8/2001 | Kasevich et al. | |
| 6,277,113 B1 | 8/2001 | Berube | |
| 6,289,249 B1 | 9/2001 | Arndt et al. | |
| 6,290,715 B1 | 9/2001 | Sharkey et al. | |
| D449,886 S | 10/2001 | Tetzlaff et al. | |
| 6,306,132 B1 | 10/2001 | Moorman et al. | |
| 6,325,796 B1 | 12/2001 | Berube et al. | |
| 6,330,479 B1 | 12/2001 | Stauffer | |
| 6,346,104 B2 | 2/2002 | Daly et al. | |
| 6,347,251 B1 | 2/2002 | Deng | |
| 6,350,262 B1 | 2/2002 | Ashley | |
| 6,355,033 B1 | 3/2002 | Moorman et al. | |
| 6,364,876 B1 | 4/2002 | Erb et al. | |
| D457,958 S | 5/2002 | Dycus et al. | |
| D457,959 S | 5/2002 | Tetzlaff et al. | |
| 6,383,182 B1 | 5/2002 | Berube et al. | |
| 6,405,733 B1 | 6/2002 | Fogarty et al. | |
| 6,471,696 B1 | 10/2002 | Berube et al. | |
| 6,496,737 B2 | 12/2002 | Rudie et al. | |
| 6,496,738 B2 | 12/2002 | Carr | |
| 6,506,189 B1 | 1/2003 | Rittman | |
| 6,512,956 B2 | 1/2003 | Arndt et al. | |
| 6,514,251 B1 | 2/2003 | Ni et al. | |
| 6,530,922 B2 | 3/2003 | Cosman et al. | |
| 6,564,806 B1 | 5/2003 | Fogarty et al. | |
| 6,569,159 B1 | 5/2003 | Edwards et al. | |
| 6,582,426 B2 | 6/2003 | Moorman et al. | |
| 6,589,234 B2 | 7/2003 | Lalonde et al. | |
| 6,592,579 B2 | 7/2003 | Arndt et al. | |
| 6,622,731 B2 | 9/2003 | Daniel et al. | |
| 6,663,624 B2 | 12/2003 | Edwards et al. | |
| 6,675,050 B2 | 1/2004 | Arndt et al. | |
| 6,685,700 B2 | 2/2004 | Behl et al. | |
| 6,699,241 B2 * | 3/2004 | Rappaport et al. | 606/33 |
| 6,706,040 B2 | 3/2004 | Mahon et al. | |
| 6,722,371 B1 | 4/2004 | Bush et al. | |
| 6,752,154 B2 | 6/2004 | Fogarty et al. | |
| 6,752,767 B2 | 6/2004 | Turovskiy et al. | |
| D496,997 S | 10/2004 | Dycus et al. | |
| D499,181 S | 11/2004 | Dycus et al. | |
| 6,823,218 B2 | 11/2004 | Berube | |
| 6,852,091 B2 | 2/2005 | Edwards et al. | |
| 6,878,147 B2 | 4/2005 | Prakash et al. | |
| D525,361 S | 7/2006 | Hushka | |
| 7,108,696 B2 | 9/2006 | Daniel et al. | |
| D531,311 S | 10/2006 | Guerra et al. | |
| 7,115,126 B2 | 10/2006 | Berube et al. | |
| 7,128,739 B2 | 10/2006 | Prakash et al. | |
| D533,942 S | 12/2006 | Kerr et al. | |
| 7,147,632 B2 | 12/2006 | Prakash et al. | |
| D535,027 S | 1/2007 | James et al. | |
| 7,174,217 B2 | 2/2007 | Rioux et al. | |
| 7,190,989 B1 | 3/2007 | Swanson et al. | |
| D541,418 S | 4/2007 | Schechter et al. | |
| 7,207,985 B2 | 4/2007 | Duong et al. | |
| D541,938 S | 5/2007 | Kerr et al | |
| 7,217,282 B2 | 5/2007 | Ginsburg et al. | |
| 7,229,437 B2 | 6/2007 | Johnson et al. | |
| 7,231,259 B2 | 6/2007 | Jenney et al. | |
| 7,234,225 B2 | 6/2007 | Johnson et al. | |
| 7,234,977 B2 | 6/2007 | Westlund et al. | |
| 7,235,070 B2 | 6/2007 | Vanney | |
| 7,238,166 B2 | 7/2007 | Callister | |
| 7,238,184 B2 | 7/2007 | Megerman et al. | |
| 7,238,194 B2 | 7/2007 | Monstadt et al. | |
| 7,241,293 B2 | 7/2007 | Davison | |
| 7,244,254 B2 | 7/2007 | Brace et al. | |
| 7,245,955 B2 | 7/2007 | Rashidi | |
| 7,264,619 B2 | 9/2007 | Venturelli | |
| 7,270,656 B2 | 9/2007 | Gowda et al. | |
| 7,270,658 B2 | 9/2007 | Woloszko et al. | |
| 7,270,659 B2 | 9/2007 | Ricart et al. | |
| 7,270,661 B2 | 9/2007 | Dahla et al. | |
| 7,270,662 B2 | 9/2007 | Visram et al. | |
| 7,271,363 B2 | 9/2007 | Lee et al. | |
| 7,273,480 B2 | 9/2007 | Young et al. | |
| 7,276,061 B2 | 10/2007 | Schaer et al. | |
| 7,282,049 B2 | 10/2007 | Orszulak et al. | |
| 7,285,116 B2 | 10/2007 | de la Rama | |
| 7,293,562 B2 | 11/2007 | Malecki et al. | |

| | | | |
|---|---|---|---|
| 7,300,438 B2 | 11/2007 | Falwell et al. | |
| 7,301,131 B2 | 11/2007 | Gauthier et al. | |
| 7,306,592 B2 | 12/2007 | Morgan et al. | |
| 7,309,325 B2 | 12/2007 | Mulier et al. | |
| 7,309,336 B2 | 12/2007 | Ashley et al. | |
| 7,311,702 B2 | 12/2007 | Tallarida et al. | |
| 7,311,703 B2 * | 12/2007 | Turovskiy et al. | 606/33 |
| 7,311,705 B2 | 12/2007 | Sra | |
| 7,317,949 B2 | 1/2008 | Morrison et al. | |
| 7,318,822 B2 | 1/2008 | Darmos et al. | |
| 7,318,823 B2 | 1/2008 | Sharps et al. | |
| 7,318,824 B2 | 1/2008 | Prakash et al. | |
| 7,319,904 B2 | 1/2008 | Cross, Jr. et al. | |
| 7,326,204 B2 | 2/2008 | Paul et al. | |
| 7,326,205 B2 | 2/2008 | Paul et al. | |
| 7,326,206 B2 | 2/2008 | Paul et al. | |
| 7,331,957 B2 | 2/2008 | Woloszko et al. | |
| 7,337,009 B2 | 2/2008 | Schell | |
| D564,662 S | 3/2008 | Moses et al. | |
| 2001/0001819 A1 | 5/2001 | Lee et al. | |
| 2001/0008966 A1 | 7/2001 | Arndt et al. | |
| 2001/0020178 A1 | 9/2001 | Arndt et al. | |
| 2001/0020180 A1 | 9/2001 | Arndt et al. | |
| 2001/0037812 A1 | 11/2001 | Dobak, III et al. | |
| 2002/0022832 A1 | 2/2002 | Mikus et al. | |
| 2002/0087151 A1 | 7/2002 | Mody et al. | |
| 2002/0133148 A1 | 9/2002 | Daniel et al. | |
| 2002/0147444 A1 | 10/2002 | Shah et al. | |
| 2002/0198520 A1 | 12/2002 | Coen et al. | |
| 2003/0004506 A1 | 1/2003 | Messing | |
| 2003/0065317 A1 | 4/2003 | Rudie et al. | |
| 2003/0069578 A1 | 4/2003 | Hall et al. | |
| 2003/0078573 A1 | 4/2003 | Truckai et al. | |
| 2003/0088242 A1 | 5/2003 | Prakash et al. | |
| 2003/0109862 A1 | 6/2003 | Prakash et al. | |
| 2003/0195499 A1 | 10/2003 | Prakash et al. | |
| 2004/0078038 A1 | 4/2004 | Desinger et al. | |
| 2004/0167517 A1 | 8/2004 | Desinger et al. | |
| 2004/0168692 A1 | 9/2004 | Fogarty et al. | |
| 2004/0243200 A1 | 12/2004 | Turner et al. | |
| 2004/0267156 A1 | 12/2004 | Turovskiy et al. | |
| 2005/0015081 A1 | 1/2005 | Turovskiy et al. | |
| 2005/0065508 A1 | 3/2005 | Johnson et al. | |
| 2005/0085881 A1 | 4/2005 | Prakash et al. | |
| 2005/0107783 A1 | 5/2005 | Tom et al. | |
| 2005/0148836 A1 | 7/2005 | Kleen et al. | |
| 2005/0159741 A1 | 7/2005 | Paul et al. | |
| 2006/0116673 A1 | 6/2006 | Gauthier et al. | |
| 2006/0259024 A1 | 11/2006 | Turovskiy et al. | |
| 2006/0264923 A1 | 11/2006 | Prakash et al. | |
| 2006/0282069 A1 | 12/2006 | Prakash et al. | |
| 2007/0027451 A1 | 2/2007 | Desinger et al. | |
| 2007/0073282 A1 | 3/2007 | McGaffigan et al. | |
| 2007/0123765 A1 | 5/2007 | Hetke et al. | |
| 2007/0129715 A1 | 6/2007 | Eggers et al. | |
| 2007/0135879 A1 | 6/2007 | McIntyre et al. | |
| 2007/0142829 A1 | 6/2007 | Ahn et al. | |
| 2007/0149964 A1 | 6/2007 | Kawabata et al. | |
| 2007/0156048 A1 | 7/2007 | Panescu et al. | |
| 2007/0156128 A1 | 7/2007 | Jimenez | |
| 2007/0156132 A1 | 7/2007 | Drysen | |
| 2007/0156133 A1 | 7/2007 | McDaniel et al. | |
| 2007/0161977 A1 | 7/2007 | Moorman et al. | |
| 2007/0173680 A1 | 7/2007 | Rioux et al. | |
| 2007/0173798 A1 | 7/2007 | Adams et al. | |
| 2007/0173812 A1 | 7/2007 | Bonan et al. | |
| 2007/0179375 A1 | 8/2007 | Fuimaono et al. | |
| 2007/0179497 A1 | 8/2007 | Eggers et al. | |
| 2007/0185478 A1 | 8/2007 | Cosentino | |
| 2007/0191825 A1 | 8/2007 | Cronin et al. | |
| 2007/0203551 A1 | 8/2007 | Cronin et al. | |
| 2007/0208334 A1 | 9/2007 | Woloszko et al. | |
| 2007/0208335 A1 | 9/2007 | Woloszko et al. | |
| 2007/0208383 A1 | 9/2007 | Williams | |
| 2007/0213700 A1 | 9/2007 | Davison et al. | |
| 2007/0213703 A1 | 9/2007 | Naam et al. | |
| 2007/0215163 A1 | 9/2007 | Harrington et al. | |
| 2007/0219551 A1 | 9/2007 | Honour et al. | |
| 2007/0225701 A1 | 9/2007 | O'Sullivan | |
| 2007/0233057 A1 | 10/2007 | Konishi | |
| 2007/0244529 A1 | 10/2007 | Choi et al. | |
| 2007/0250053 A1 | 10/2007 | Fernald et al. | |
| 2007/0250054 A1 | 10/2007 | Drake | |
| 2007/0250055 A1 | 10/2007 | Johnson et al. | |
| 2007/0250056 A1 | 10/2007 | Vanney | |
| 2007/0255276 A1 | 11/2007 | Silwa, Jr. et al. | |
| 2007/0260235 A1 | 11/2007 | Podhajsky | |
| 2007/0260237 A1 | 11/2007 | Sutton et al. | |
| 2007/0270679 A1 | 11/2007 | Nguyen et al. | |
| 2007/0270791 A1 | 11/2007 | Wang et al. | |
| 2007/0276361 A1 | 11/2007 | Stevens-Wright et al. | |
| 2007/0276362 A1 | 11/2007 | Rioux et al. | |
| 2007/0282323 A1 | 12/2007 | Woloszko et al. | |
| 2007/0282324 A1 | 12/2007 | Vaska et al. | |
| 2007/0282325 A1 | 12/2007 | Young et al. | |
| 2007/0287995 A1 | 12/2007 | Mayse | |
| 2007/0287998 A1 | 12/2007 | Sharareh et al. | |
| 2007/0293853 A1 | 12/2007 | Truckai et al. | |
| 2007/0293854 A1 | 12/2007 | Pless et al. | |
| 2007/0293855 A1 | 12/2007 | Sliwa, Jr. et al. | |
| 2007/0299488 A1 | 12/2007 | Carr | |
| 2008/0004614 A1 | 1/2008 | Burdette et al. | |
| 2008/0004618 A1 | 1/2008 | Johnson et al. | |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 667 126 | 8/1995 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 10/1961 |

| | | |
|---|---|---|
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO 93/20767 | 10/1993 |
| WO | WO 93/20768 A1 | 10/1993 |
| WO | WO 96/34571 | 11/1996 |
| WO | WO 9741800 | 11/1997 |
| WO | WO 97/48449 | 12/1997 |
| WO | WO 97/48450 | 12/1997 |
| WO | WO 97/48451 | 12/1997 |
| WO | WO 99/56642 | 11/1999 |
| WO | WO 99/56643 | 11/1999 |
| WO | WO 99/56812 | 11/1999 |
| WO | WO00/47283 | 8/2000 |
| WO | WO 00/49957 | 8/2000 |
| WO | WO 00/57811 | 10/2000 |
| WO | WO 01/60235 | 8/2001 |
| WO | WO 02/078777 | 10/2002 |
| WO | WO03/024309 | 3/2003 |
| WO | WO 03/034932 | 5/2003 |
| WO | WO 03/039385 | 5/2003 |
| WO | WO 03/047043 A1 | 6/2003 |
| WO | WO 03/088806 | 10/2003 |
| WO | WO 03/088858 | 10/2003 |
| WO | WO 2005/011049 | 2/2005 |

OTHER PUBLICATIONS

I Chou, C.K., "Radiofrequency Hyperthermia in Cancer Therapy," Biologic Effects of Nonionizing Electromagnetic Fields, Chapter 94, CRC Press, Inc., (1995), pp. 1424/1428.
Urologix, Inc./Medical Professionals: Targis3 Technology http://www.urologix.com/medical/technology.html (total pp. 3), Apr. 27, 2001.
International Search Report—EP 06 00 9435 dated Jul. 13, 2006.
U.S. Appl. No. 08/483,742, filed Jun. 7, 1995, Stern et al.
U.S. Appl. No. 08/136,098, filed Oct. 14, 1993, Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds In Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite-Element Codes To Model Electrical Heating And Non-LInear Thermal Transport In Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College Of Surgeons (ACS) Clinic La Congress Poster (2000).

Johnson et al., "New Low-Profile Applicators for Local Heating of Tissues", IEEE Transactions on Biomedical Engineering, vol. BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics Figo World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/1977).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08012829.1 dated Oct. 29, 2008.
European Search Report EP 08015842 dated Dec. 5, 2008.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
US 5,326,343, 07/1994, Rudie et al. (withdrawn)

* cited by examiner

STEP 450 — REMOVE INNER CONDUCTOR FROM FEEDLINE/COAXIAL CABLE

STEP 451 — FORM FIRST ASSEMBLY BY REMOVING INSULATION FROM DISTAL PORTION OF FEEDLINE/COAXIAL CABLE

STEP 452 — FORM SECOND ASSEMBLY BY JOINING HELICAL ANTENNA MEMBER AND RIGID MEMBER

STEP 453 — FORM STRUCTURALLY RIGID HELICAL ANTENNA BY JOINING FIRST AND SECOND ASSEMBLIES

*FIG. 7G*

COOLED HELICAL ANTENNA FOR MICROWAVE ABLATION

BACKGROUND

1. Technical Field

The present disclosure relates generally to medical/surgical ablation, devices, assemblies and methods of their use. More particularly, the present disclosure relates to cooled microwave antenna assemblies comprising a helical antenna configured for direct insertion into tissue for diagnosis and treatment of the tissue and methods of using the same.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control. This is partly why a more direct and precise method of applying microwave radiation has been sought.

Presently, there are several types of microwave probes in use, e.g., monopole, dipole, and helical. One type is a monopole antenna probe, which consists of a single, elongated microwave conductor exposed at the end of the probe. The probe is sometimes surrounded by a dielectric sleeve. The second type of microwave probe commonly used is a dipole antenna, which consists of a coaxial construction having an inner conductor and an outer conductor with a dielectric separating a portion of the inner conductor and a portion of the outer conductor. The third type of microwave probe commonly used is a helical antenna. Helical antennas are typically composed of a single driven element, or conducting wire, coiled in a spiral, or helix. In the monopole and dipole antenna probe, microwave energy generally radiates perpendicularly from the axis of the conductor. Helical antenna may radiate in a normal mode, in which the radiation pattern is similar to that of an electrically short dipole or monopole or the helical antenna may radiate in the axial mode, in which the radiation pattern is circular.

SUMMARY

The present disclosure relates generally to microwave antenna assemblies and methods of their use, e.g., in tissue ablation applications. More particularly, the present disclosure relates to a cooled microwave antenna assemblies containing a helical antenna. The microwave antenna assembly may be structurally robust for direct insertion into tissue, without the need for additional introducers or catheters, for diagnosis and treatment of the tissue.

A microwave antenna assembly of the present disclosure includes an elongate cooling jacket having proximal and distal ends and an inner lumen defined therebetween and a helical microwave antenna member disposed within at least a portion of the elongated cooling jacket. Helical microwave antenna includes an inner and outer conductor, the inner conductor disposed within the outer conductor. At least a portion of the inner conductor extends distally from the outer conductor and forms a plurality of loops; wherein at least two loops of the plurality of loops forms an electrical connection therebetween. At least a portion of the plurality of loops is configured to deliver microwave energy.

The microwave antenna assembly may further include a rigid member that supports the helical microwave antenna, wherein the rigid member engages the distal portion of the outer conductor. The rigid member may define a lumen therewithin and at least a portion of the inner conductor of the helical microwave antenna may be disposed within the lumen of the rigid member. At least one loop of the helical microwave antenna member may be disposed on the periphery of the rigid member. The transverse cross-section of a portion of the inner conductor disposed within the outer conductor may be different than a transverse cross section of the inner conductor that extends distally from the outer conductor. The rigid member may be formed of a dielectric material.

The microwave antenna assembly may further include a sharpened tip adapted to penetrate tissue and attached to the distal end of the elongated cooling jacket forming a fluid-tight seal therewith. Microwave antenna assembly may include at least one inflow tube for supplying cooling fluid to the distal end of the elongated cooling jacket.

The inner conductor of the microwave antenna assembly may further include a feedline conductive member and a helical conductive member. The distal end of the feedline conductive member connects to the proximal end of the helical conductive member. A substantial portion of the feedline conductive member may be disposed within the outer conductor with a substantial portion of the helical conductive member distal the outer conductor. The transverse cross-section of the feedline conductive member may be different that a transverse cross-section of the helical conductive member.

The elongated cooling jacket of the microwave antenna assembly may include a dielectric material. Alternatively, the elongated cooling jacket may include a proximal jacket portion and a distal jacket portion. The distal jacket portion may be disposed between, and attached to, the proximal jacket portion and the sharpened tip. The distal jacket portion may be formed of a dielectric material and the proximal jacket portion may be formed of a conductive material. A plurality of the at least two loops of the helical microwave antenna member may be disposed within the distal jacket portion of the elongate cooling jacket. The microwave antenna assembly may further include a coating disposed on an outer surface thereof and configured to prevent tissue from sticking thereto.

In yet another embodiment of the present disclosure a helical microwave antenna includes a first and second assembly. The first assembly includes a tubular outer conductor defining a longitudinal lumen therethrough and an insulating member, disposed within at least a portion of the outer conductor and defining a longitudinal lumen therewithin. The second assembly includes an elongated conductive member forming a helical loop portion and a feedline portion and a rigid member defining a lumen therewithin. The lumen of the rigid member adapted to receive at least a portion of the elongated conductive member, wherein the helical loop portion of the elongated conductive member is disposed on the periphery of a distal portion of the rigid member and at least a portion of the feedline portion extends proximally from the rigid member. The proximal portion of the second assembly is adapted to engage a distal portion of the first assembly with at least a portion of the feedline portion of the elongated conductive member disposed within the lumen of the insulating member.

The outer conductor of the first assembly may engage the rigid member of the second assembly. Engagement may be formed by at least one of a press fit engagement, a threaded engagement, a taper lock engagement and a chemical engagement.

In yet another embodiment of the present disclosure, a microwave antenna assembly includes a feedline configured to supply microwave energy, a helical microwave antenna connected to a distal end of the feedline, the helical microwave antenna being configured to transmit microwave energy; and a rigid member supporting the helical microwave antenna, wherein at least a portion of the rigid member engages the feedline and is partially disposed therewithin.

In yet another embodiment of the present disclosure, a method of forming a helical antenna member includes the steps of removing an inner conductor of a microwave antenna feedline, removing a portion of insulation from a distal portion of the microwave antenna feedline, forming a helical microwave antenna including a feedline portion and a helical portion, providing a rigid member configured to receive a helical microwave antenna, joining the helical microwave antenna and the rigid member wherein the helical portion of the helical microwave antenna substantially surrounds at least a portion of the rigid member and at least a portion of the feedline portion extends proximally from the rigid member, and joining the distal end of the microwave antenna feedline with the proximal end of the rigid member wherein at least a portion of the helical antenna member is disposed within a lumen defined in the rigid member and at least a portion of the feedline portion of the helical antenna member is disposed within the microwave antenna feedline. The feedline portion may be formed from a first elongate conductive member and the helical portion of the helical microwave antenna is formed from a second elongate conductive member.

BRIEF DESCRIPTION OF THE DRAWINGS

FIG. 7G is a flowchart of the steps in the formation of the structurally rigid helical antenna assembly of FIG. 6B;

DETAILED DESCRIPTION OF EMBODIMENTS

Figure 1:
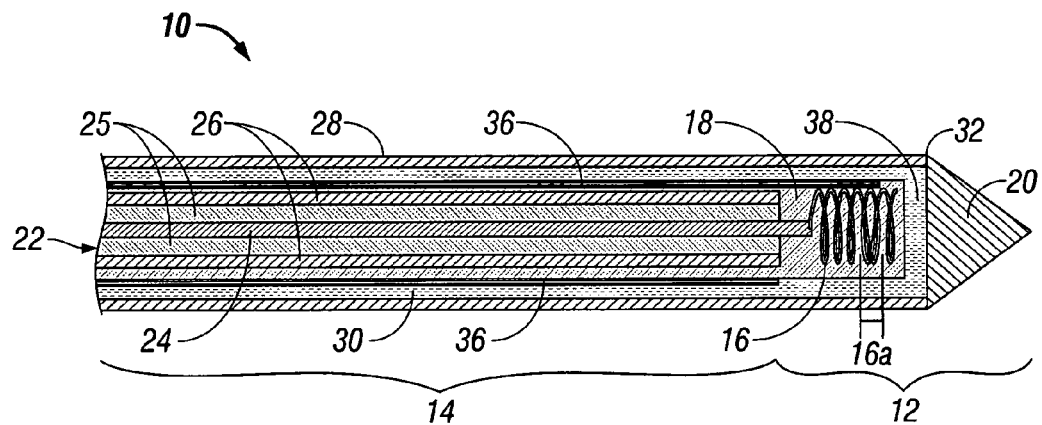
FIG. 1 is a cross-sectional side view of a distal end of a cooled helical microwave antenna assembly according to an embodiment of the present disclosure.

Embodiments of the presently disclosed microwave antenna assembly will now be described in detail with reference to the drawing figures wherein like reference numerals identify similar or identical elements. As used herein and as is traditional, the term "distal" refers to the portion that is furthest from the user and the term "proximal" refers to the portion that is closest to the user. In addition, terms such as "above", "below", "forward", "rearward", etc. refer to the orientation of the figures or the direction of components and are simply used for convenience of description.

During invasive treatment of diseased areas of tissue in a patient the insertion and placement of an electrosurgical energy delivery apparatus, such as a microwave antenna assembly, relative to the diseased area of tissue is important for successful treatment. The size and dimension of the ablation area created by a microwave antenna is dependant, among other factors, on the type of microwave antenna. Clinicians should therefore select a microwave antenna capable of generating an ablation region greater than the size and dimension of the target tissue and insert the microwave antenna such that the ablation region created by the microwave antenna includes the target tissue.

Dipole and monopole microwave antennas typically form oblong or tear-shaped ablation regions. The helical antennas of the present disclosure may create near spherical ablation regions while other helical antennas of the present disclosure with different geometries may create ablation regions similar in shape to those created by a dipole or monopole antennas, thereby allowing a clinician to select a microwave antenna that creates an appropriate ablation region for each individual target tissue area.

Cooled Helical Antennas

Figure 2:
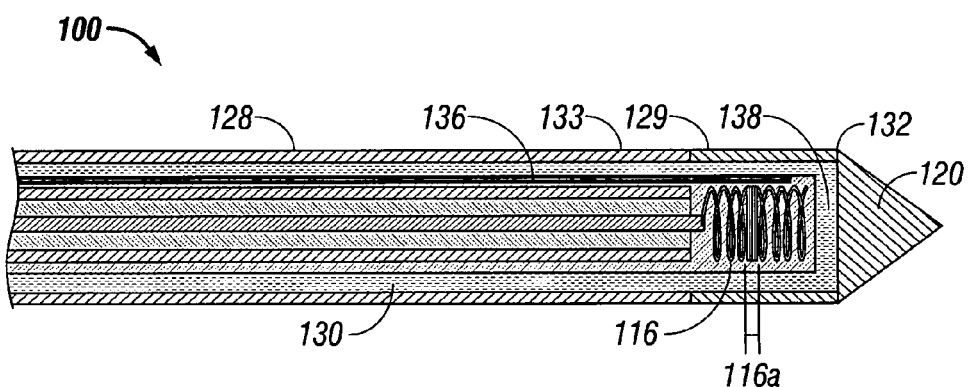
FIG. 2 is a cross-sectional side view of a distal end of a cooled helical microwave antenna assembly of FIG. 1 including a double cooling jacket.

Referring now to FIGS. 1-2, a microwave antenna assembly, according to an embodiment of the present disclosure, is shown as 10. The microwave antenna assembly 10 includes an antenna portion 12 and a feedline portion 14 operatively connected to and supporting antenna portion 12. Antenna portion 12 includes a helical antenna member 16, antenna insulation 18 surrounding the exterior of antenna member 16, and a sharpened distal tip 20. Feedline portion 14 includes a coaxial feedline 22 including an inner conductor 24 electrically connected to antenna member 16, and an outer conductor 26 overlying at least a portion of inner conductor 24 and at least partially separated therefrom by a feedline insulation 25.

Microwave antenna assembly 10 includes a cooling jacket 28 surrounding at least a segment of feedline portion 14 and at least a segment of antenna portion 12. Cooling jacket 28 connects to sharpened distal tip 20 at contact area 32 and forms a fluid-tight seal around a cooling chamber 30 (i.e., the space defined between an outer surface of feedline portion 14 and/or antenna portion 12 and an inner surface of cooling jacket 28). Fluid-tight seal at contact area 32 may be formed by means of an interference fit, a screw junction, various shaped slip fit connections, adhesive, soldering, crimping or other suitable methods for joining two members.

Cooling jacket 28 is made of an insulating material, such as, for example, a polyimide or similar dielectric material, to avoid shielding microwave radiation around antenna member 16. The outer surface of cooling jacket 28 may also be coated with a suitable lubricious substance to aid in the movement of cooling jacket 28 in or through tissue as well as to aid in preventing tissue from sticking to the outer surface thereof. The coating itself may be made from suitable materials, e.g., polymers, etc.

Microwave antenna assembly 10 includes one or more inflow tubes 36 to supply cooling fluid to a distal portion 38 of cooling chamber 30. Inflow tubes 36 may include thin-walled polyimide tubes. In operation, a pump (not explicitly shown) supplies cooling fluid (e.g., saline, water or other suitable cooling fluid) to one or more inflow tubes 36 which, in turn, deliver cooling fluid to the distal portion 38 of cooling chamber 30. Inflow tubes 36 may be held in place along cooling jacket 28 by using UV adhesive or other similar suitable adhesives, as well as heat shrink tubing or by other suitable methods.

Cooling fluid flows through the cooling chamber 30, away from the distal end of microwave antenna assembly 10 to a proximal end thereof, to absorb energy and exists through a cooling fluid return or tube (not explicitly shown). Cooling chamber 30 supplies cooling fluid to feedline 22, thus limiting shaft burn and the length of the ablation area around antenna, limiting tissue charring, maximizing energy transfer from the generator to the antenna and allowing for a larger radius of ablation area.

The outer diameter of the cooling jacket 28 defines the cross-sectional size of the microwave antenna assembly 10. The diameter of the cooling jacket 28 should be small enough to limit the invasiveness of a procedure performed with microwave antenna assembly 10. The diameter of the helical antenna member must be small enough to fit inside cooling jacket 28 and to allow for adequate cooling therearound. Helical antenna member 16 may have a helix diameter of between about 0.030" and about 0.060", which allows for a diameter of cooling jacket 28 to be between about 0.080" and about 0.095".

A proximal end of feedline 22 connects microwave antenna assembly 10 to an electrosurgical power generating source (not explicitly shown), e.g., a generator or other suitable source of radio frequency energy and/or microwave energy, and supplies electrosurgical energy to antenna member 16 of the microwave antenna assembly 10. In operation, during initial insertion into tissue, microwave antenna assembly 10 defines a path through the tissue by virtue of the mechanical geometry of sharpened distal tip 20, and, if needed, by the application of energy to tissue, e.g. electrical, mechanical or electromechanical energy.

Feedline 22 may be formed from a suitable flexible, semi-rigid or rigid microwave conductive cable and may connect directly to an electrosurgical power generating source. Alternatively, feedline 22 may connect to a connector (not shown) capable of conducting electrosurgical energy and configured to connect to an electrosurgical power generation source (not shown) via an electrical cable (not shown).

Feedline insulation 25 may be disposed between inner conductor 24 and outer conductor 26 to provide insulation therebetween. Feedline insulation 25 may be any suitable dielectric or low loss material, such as, for example, low density, ultra-low density PTFE, or equivalent material including air. As described hereinbelow, at least a portion of the feedline insulation 25 may be removed and/or replaced with a portion of the antenna insulation 18 or other suitable member that reinforces or strengthens feedline 22 and/or antenna member 16.

Inner conductor 24, outer conductor 26 and/or antenna member 16 may be formed of suitable conductive material including, and not limited to, copper, gold, silver or other conductive metals having similar conductivity values. Alternatively, inner conductor 24, outer conductor 26 and/or antenna member 16 may be constructed from stainless steel or may be plated with other materials, e.g., other conductive materials, such as gold or silver, to improve their respective properties, e.g., to improve conductivity, decrease energy loss, etc.

As described hereinbelow, inner conductor 24 may be removed and replaced with a suitable inner conductor (not shown) having an antenna member 16 disposed on or about the distal end thereof.

Antenna member 16 may be formed from an elongated conductive member shaped into a helical configuration. Antenna member 16 may be formed from a portion of the inner conductor 24 that extends distal of the feedline portion 14 into the antenna portion 12. Alternatively, antenna member 16 may be formed from a separate elongated conductive member and attached to inner conductor 24, outer conductor 26 or both using suitable attachment methods like soldering, crimping or other suitable methods used to attach two elongated conductors.

The transverse cross-sectional profile of antenna member 16 may be different from the transverse cross-sectional profile of the inner conductor 24. For example, transverse cross-sectional profile of the helical antenna 26 may be selected to facilitate the formation of a helical shape while the transverse cross-sectional profile of the inner conductor 24 may be substantially circular. The transverse cross-sectional profile of antenna member 16 may include a cross-sectional profile having with at least one partially flat surface. The at least one partially flat surface may mechanically aid in the formation of the helical shape. Alternatively, the at least one partially flat surface may provide a contact surface for the adjacent loops of the helical antenna member 16 to make contact with each other.

The transverse cross-sectional profile, shape and dimension of the antenna member 16 may influence the operative properties of the microwave antenna and affect the ability of the microwave antenna to deliver energy.

The transverse cross-sectional profile of the antenna member 16 may be altered during the formation of the antenna member 16. For example, prior to the formation of antenna member 16 the transverse cross-sectional shape of the material forming antenna member 16 may have a first transverse cross-sectional profile (e.g., circular or rectangular). Upon the formation of helical antenna 16, or upon a compression of helical antenna 16 after formation, the first transverse cross-sectional profile of the material may change to a second transverse cross-sectional profile.

A layer of antenna insulation 18 (e.g., 0.0025"-0.005" PET, PTFE or similar material) is placed around helical antenna member 16 to completely insulate antenna member 16 from cooling fluid. The thickness and type of antenna insulation 18 may also be selected to effectively match the impedance of the antenna member 16 to tissue. Other means of insulating antenna member 16 from cooling water may be used, such as, for example, to surround antenna member 16 with adhesive, epoxy or similar materials At least two of the loops forming helical antenna member 16 are in electrical contact with each other, at one contact point, thereby forming a loop contact area 16a. As illustrated in FIG. 2, contact between the two or more loops in the loop contact area 116a may be achieved by simply wrapping the loops of the helix in close proximity to one another or the loops may be compressed to create contact between one or more loops. Various transverse cross-sectional profiles may also be selected to achieve contact between one or more loops. Elongated material that forms the helical antenna member 16, 116 may have one or more flat surfaces to increase the electrical contact surface between the plurality of helical loops. The axial position of the loop contact area 16a, 116a along the helical antenna member 16, 116 may vary. For example, the loop contact area of FIG. 1 is located toward the middle or distal portion of the helical antenna member 16 and the loop contact area 116a of FIG. 2 is located toward the middle of the helical antenna member 116. The loop contact area may be located at various axial locations on the helical antenna member as illustrated in other embodiments contained herewithin.

The figures herewithin are illustrative of the various embodiments and should not be construed as limiting. For example, FIG. 1 illustrates a helical antenna member 16 with six helical loops and a loop contact area 16a including two loops and FIG. 2 illustrates a helical antenna member 116 with eleven helical loops and a loop contact area 116a including four loops. The actual number of loops in the helical antenna and the actual number of loops in the loop contact area may include any number of loops based on the selected properties of the helical antenna. The selected properties may include generator frequency, required ablation size, required ablation dimensions and microwave assembly dimension. Contact between loops may be any include any suitable contact, such as for example, a single point, a single tangential point or a plurality of points along an arcuate length.

The plurality of wraps or loops of the helical antenna member 16 may be axially compressed to allow at least one or more of the helical loops to make electrical contact with each other. The transverse cross-sectional profile of the material that forms the helical antenna member 16 may vary along its length to influence the properties of the helical antenna member 16 and to suitably match the helical antenna member 16 to the target tissue.

Turning now to FIG. 2, another embodiment of a microwave antenna assembly in accordance with the present disclosure is designated as 100. Microwave antenna assembly 100 is substantially similar to microwave antenna assembly 10 and thus will only be described herein to the extent necessary to identify differences in construction and operation. Microwave antenna assembly 100 includes a shaft cooling jacket 128 and an antenna cooling jacket 129. Distal end of antenna cooling jacket 129 forms a fluid-tight seal with sharpened distal tip 120 at contact area 132. Proximal end of antenna cooling jacket 129 forms a fluid-tight seal with shaft cooling jacket 128 at contact area 133. The fluid-tight seals at contact areas 132, 133 may be formed by means of an interference fit, a screw junction, various shaped slip fit connections, adhesive, soldering, crimping or other suitable methods for joining and sealing two members.

As mentioned above, loop contact area 116a of FIG. 2 is located near the middle of the helical antenna member 116. The pitch, or distance between adjacent loops, in the loop contact area 116a is different than the pitch outside of the loop contact area 116a.

Shaft cooling jacket 128, antenna cooling jacket 129 and sharpened distal tip form a fluid-tight seal to define a cooling chamber 130 about at least antenna member 16 At least one inflow tube 136 supplies cooling fluid to a distal portion 138 of cooling chamber 130.

The antenna cooling jacket 129 is formed of an insulating material, such as, for example, a polyimide or similar dielectric material, to avoid shielding microwave radiation around antenna member 116. The shaft cooling jacket 128, which does not surround the antenna member 116, does not need to have insulating properties and can be formed of a suitable conductive or non conductive material, such as, for example, stainless steel hypotube, other metal or plastic tubes. It is desirable to maintain the same outer diameter for the cooling jackets 128, 129 to avoid steps along the outer surface of the device.

The outer surface of cooling jackets 128, 129 may also be coated. The coating is a suitable lubricious substance to aid in the movement of cooling jacket in tissue as well as to aid in preventing tissue from sticking to the outer surface thereof. The coating itself may be made from suitable conventional materials, e.g., polymers, etc.

Helical Antenna Geometries

Figure 3:
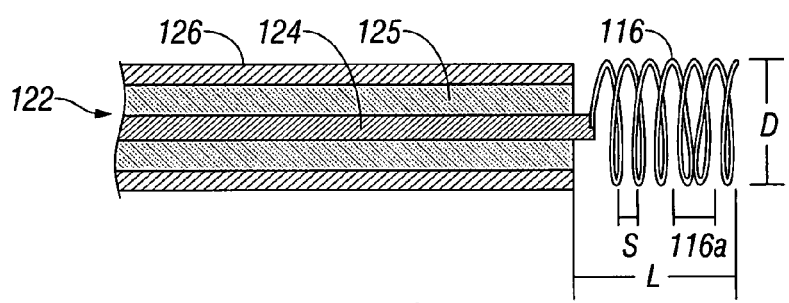
FIG. 3 is a cross-sectional side view of a distal end of the cooled helical microwave antenna assemblies of FIGS. 1 and 2 with the cooling jacket, sharpened tip, inflow tubes and antenna insulation removed therefrom.

The microwave antenna assemblies of the present disclosure include a helical microwave antenna to create lesions in tissue. As illustrated in FIG. 3, feedline 122 includes an outer conductor 126 and an inner conductor 124 separated by insulation 125. Helical antenna member 116 may be formed of a suitable conductive member that extends distally from the feedline 122 and forms a helical or spiral geometry, including a plurality of turns, loops or wraps, with each turn, loop or wrap spaced by a pitch "S", a diameter "D", and a length of "L". The pitch "S" between two loops in electrical contact is approximately equal to zero. Antenna member 116 may be a portion of the inner conductor 124 that extends distally beyond the outer conductor 126, as illustrated in FIG. 3. Alternatively, helical antenna member 116 may be a separate elongated member that connects to the inner conductor 124, outer conductor 126 or both, as illustrated hereinbelow.

In some embodiments herein, the energy delivered and the magnetic field generated by helical antenna member 116 is dependent on several factors, including and not limited to the diameter "D", the length "L" and the pitch "S" thereof. The helical antenna member 116 radiates microwave energy at a frequency wavelength of "λ". When "D/λ" is relatively small, the helical antenna member 116 operates in a normal mode and the energy field generated by the helical antenna member 116 resembles a monopole antenna.

The optimum length "L" of helical antenna member 116 depends on the diameter "D" but can usually be selected to have a length "L" of approximately 0.4" to 0.6" for diameters "D" of approximately 0.04".

By varying the geometry of helical antenna member 116, the helical antenna member 116 may operate in a unidirectional or axial mode. Helical antennas members 116 may operate in a unidirectional or axial mode if the range of "(πD)/λ" is between about 0.75 and 1.33. At 915 Mhz and at diameters "D" of interest in an interstitial application, "D/λ" will be relatively small. Consequently, energy radiation will be similar to a monopole, e.g., perpendicular to the longitudinal axis of the helix.

In addition, in some embodiments described herewithin, the helical antenna member 116 may include a loop contact area 116a, as described above. The energy delivered and the magnetic field generated by the helical antenna member 116 may be dependant on at least one characteristic of the loop contact area 116a. For example, energy delivered and the magnetic field generated may change dependant upon: the position of the loop contact area 116a, the number and/or pitch of the loops within the loop contact area 116a, the quality and/or amount of the contact between loops and the cross-sectional area of the loops within the loop contact area 116a or any combination thereof.

A variety of methods may be used to create the loop contact area 116a. Contact between the two or more loops may occur due to the positioning of two or more loops in close proximity to each other. As illustrated in FIG. 1, the loop contact area 16a may be formed by repositioning one or more loops such that contact occurs between loops. In another method contact area may be created by deforming one or more loops, thereby increasing the width of the loops, such that contact is made between two or more loops.

In another method, the two or more loops are joined to one another by soldering, welding, brazing or any other suitable method known by one having skill in the art. Alternatively, a jumper may connect two or more loops together or other suitable methods and means may be used to connect two or more loops.

Figure 4A:
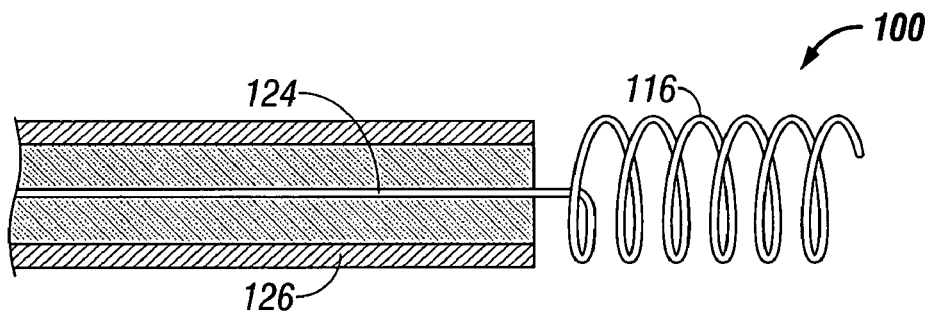
FIGS. 4A-4I are various geometries of helical-shaped antennas for use in the cooled helical antenna assemblies of FIGS. 1 and 2.
Figure 4B:
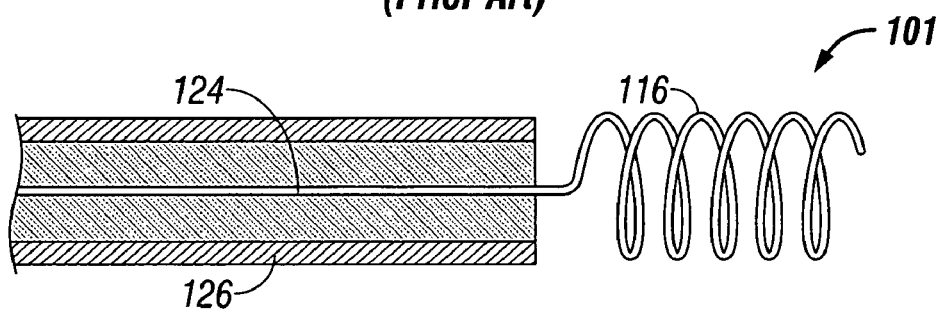
Figure 4C:
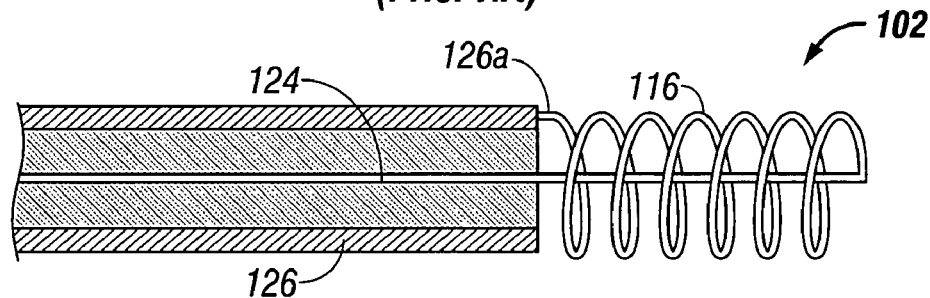

Various geometries for helical antenna members 116 are illustrated in FIGS. 4A-4F with FIGS. 4A-4C illustrating helical antenna members known in the art. FIG. 4A illustrates a microwave antenna assembly 100 including a helical antenna member 116 having a clockwise helical configuration, and FIG. 4B illustrates a microwave antenna assembly 101 including a helical antenna member 116 having a counter-clockwise helical configuration. The direction of the magnetic field generated by each microwave antenna assembly 100, 101 is dependant on the orientation of the helix of helical antenna member 116. Therefore, the energy fields generated by antennas assemblies 100, 101, with similar sizes, are opposite in direction.

Figure 4D:
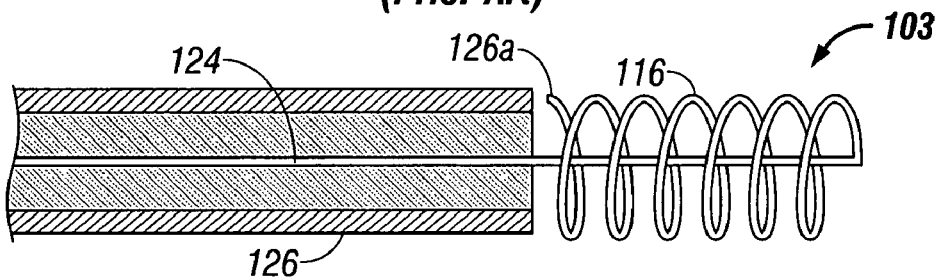

As illustrated in FIGS. 4C and 4D, respective microwave antenna assemblies 102, 103 include inner conductors 124 that contact the helical antenna member 116 at a distal end thereof. In FIG. 4C the helical antenna member 116 contacts a distal end 126a of the outer conductor 126. Alternatively, as illustrated in FIG. 4D, the helical antenna member 116 may not contact or may be spaced away from distal end 126a of outer conductor 126. Although helical antenna members 116 and inner conductors 124 are illustrated as separate elements, the inner conductors 124 and helical antenna members 116 may or may not be separate elements in any of the embodiments contained herein.

Figure 4E:
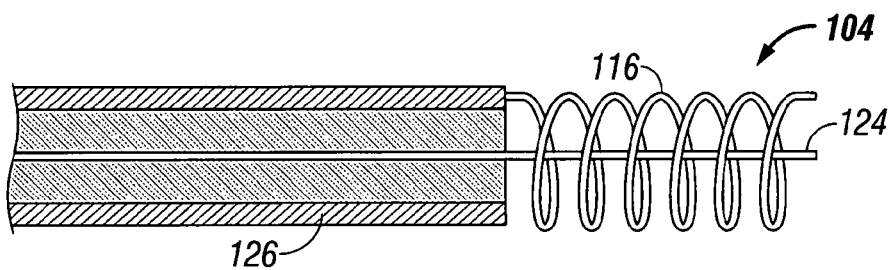
Figure 4F:
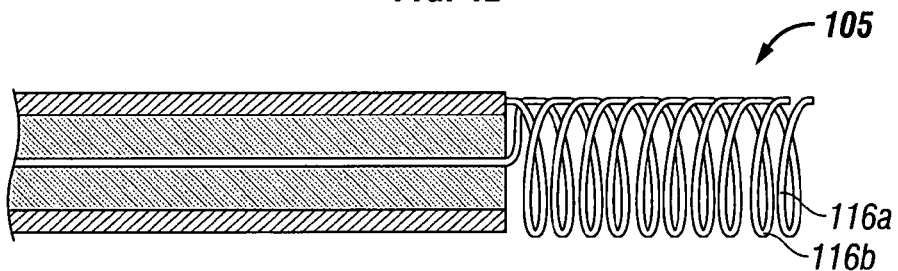

In FIG. 4E, a microwave antenna assembly 104 includes a helical antenna member 116 having a proximal end in contact with a distal end of outer conductor 126. Helical antenna member 116 is positioned radially about a portion of the inner conductor 124 that extends distally from the distal end of outer conductor 126 and is positioned substantially along the radial center of helical antenna member 116.

In FIGS. 4A-4E, the helical antenna member 116 may be modified by forming an electrical connection between two or more of the loops of the helical antenna member 116, as described and taught herewithin.

FIGS. 4F-4I illustrate respective microwave antenna assemblies 105-108 including helical antenna members 116a, 116b forming a double helix or double spirals. Each microwave antenna assembly 105-108 includes a first helical antenna member 116a oriented in a first direction, and a second helical antenna member 116b oriented in a second direction. First helical antenna member 116a is formed from, or connects to, the inner conductor 124. Second helical antenna member 116b connects to a distal end of outer conductor 126

Figure 4G:
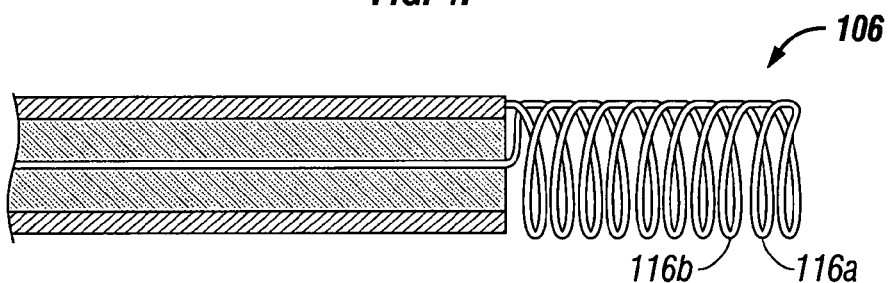
Figure 4H:
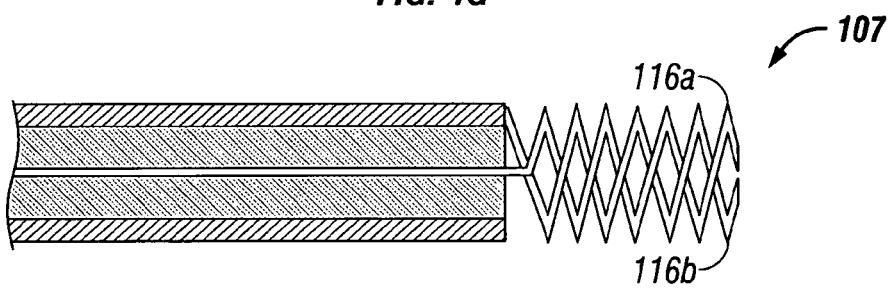
Figure 4I:
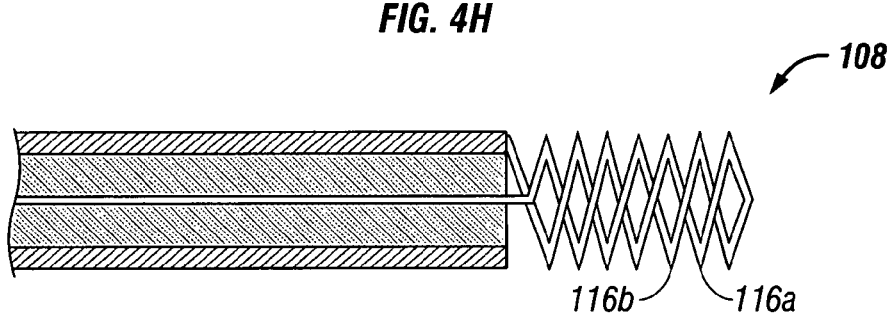

In FIGS. 4G and 4I, the distal end of first helical antenna member 116a and the distal end of second antenna member 116b connect at the distal end of microwave antenna 105, 108.

Structurally Strengthened Helical Antenna Members

Any of the aforementioned microwave antenna assemblies can be strengthened by adding rigid members inside the helix of the helical antenna members. Rigid members may be made of ceramic, hard plastic or other suitable rigid dielectric material as well as insulated metal. The rigid members may extend from the helical antenna members into the feedline to give rigidity to the entire microwave antenna assembly, to the transition point between the feedline and the helical antenna member.

Figure 5A:
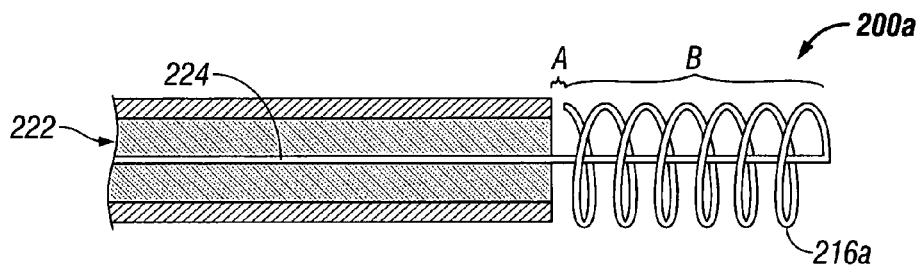
FIG. 5A is a schematic cross-sectional side view of the distal end of a helical microwave antenna assembly including the helical shaped geometry of FIG. 4D.
Figure 5B:
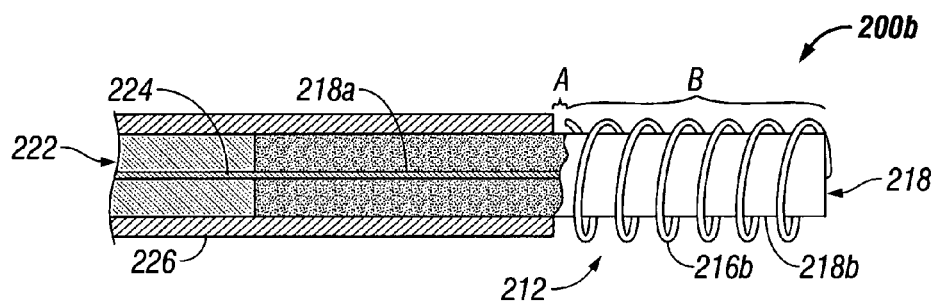
FIG. 5B is a schematic cross-sectional side view of the distal end of the helical microwave antenna assembly of FIG. 5A, having a reinforced configuration.

FIG. 5A illustrates the helical antenna member of FIG. 4D without a rigid member and FIG. 5B illustrates the helical antenna member of FIG. 4D with a rigid member 218 disposed therewithin.

As seen in FIG. 5B, a rigid member 218 may support a helical antenna member 216b of microwave antenna assembly 200b, at least a portion of the inner conductor 224 and/or at least a portion of the feedline 222. Rigid member 218 may be formed of appropriate insulating or non-conducting material provided the material is sufficiently rigid/stiff and does not materially or significantly impair the ability of the microwave antenna assembly 200b to deliver microwave energy.

With reference to FIGS. 5A and 5B, rigid member 218 provides support to microwave antenna assembly 200b at two locations "A" and "B". An inner lumen 218a, formed in the substantial radial center of rigid member 218, provides support for inner conductor 224. Helical antenna member 216b is formed or wrapped around the outer perimeter 218b of rigid member 218. Rigid member 218 aids in preservation of the helical shape and prevents deformation of helical antenna member 216b.

At least a portion of rigid member 218 may extend into feedline 222 and provide support for the distal portion of feedline 222. Rigid member 218 provides support for helical antenna member 216b and provides a transition between feedline 222 and antenna portion 212.

Rigid member 218 may have a uniform longitudinal/transverse cross-sectional area and/or dimension as illustrated in FIG. 5B. Alternatively, cross-sectional area and/or dimension of rigid member 218 may vary at one or more locations along a length thereof. For example, the portion of the rigid member 218 disposed within outer conductor 226 of feedline 222 may have a first cross-sectional area and/or dimension and the portion of rigid member 218 distal of the distal end of feedline 222 may have a second cross-sectional area and/or dimension. Alternatively, at least a portion of a length of rigid member 218 may be tapered.

Method of Forming a Rigid Helical Antenna Member

Figure 6A:
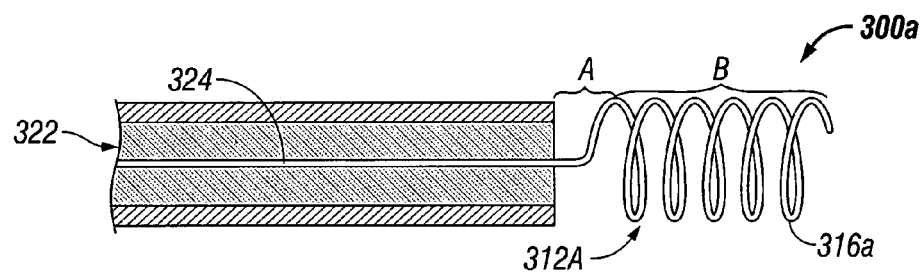
FIG. 6A is a schematic cross-sectional side view of the distal end of a helical microwave antenna assembly including the helical shaped geometry of FIG. 4B.
Figure 6B:
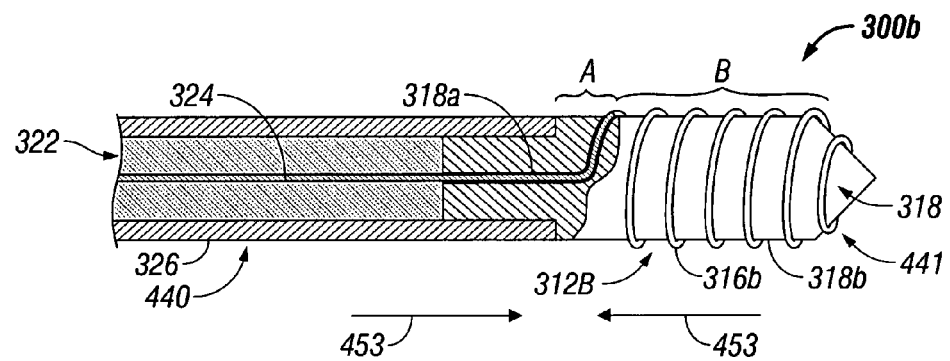
FIG. 6B is a schematic cross-sectional side view of the distal end of the helical microwave antenna assembly of FIG. 6A, having a reinforced configuration.
Figure 7A:
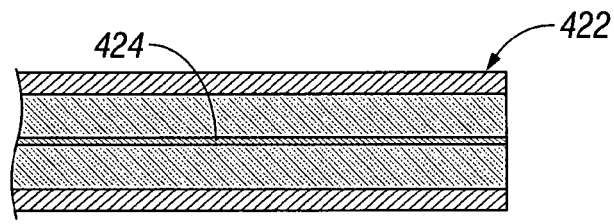
FIGS. 7A-7F illustrate a method of assembling the reinforced helical microwave antenna assembly of FIG. 6B.
Figure 7B:
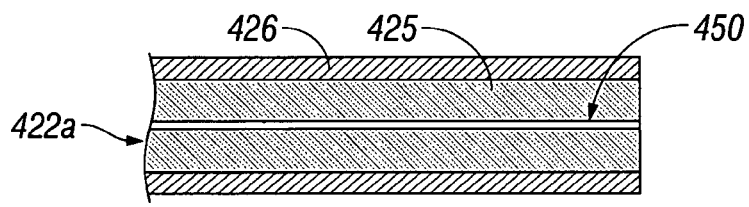
Figure 7C:
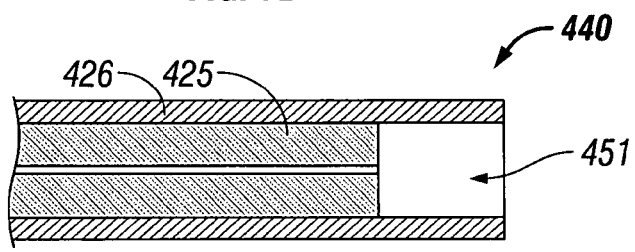
Figure 7D:
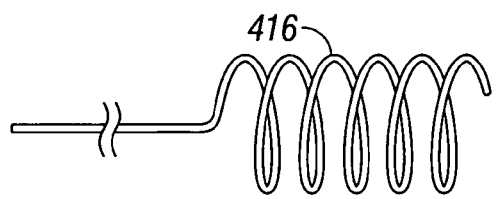
Figure 7E:
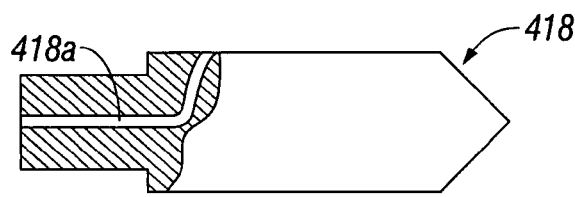
Figure 7F:
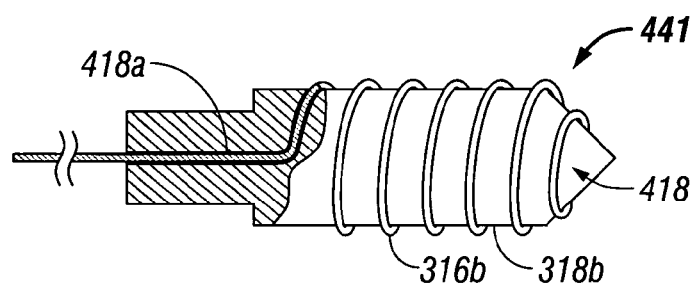

FIGS. 6A and 6B illustrate the addition of a rigid member 318 to the helical antenna member 101 of FIG. 4B. As illustrated in FIG. 6A, in the proximal portion "A" of the helical antenna member 316a, the inner conductor 224 transitions from the center of the feedline 322 to the proximal end of helical portion of the antenna portion 312a.

FIG. 6B illustrates a structural rigid helical antenna assembly 330b formed from the helical antenna member 300a of FIG. 6A and including a rigid member 318 disposed therewithin. Rigid member 318 may provide a transition between the feedlines 222 and the antenna 312b and may provide strength to portions "A" and "B" of the antenna 312a, 312b. At least a portion of rigid member 318 is disposed within outer conductor 326 of feedline 322 and a portion of rigid member 318 extends beyond the distal portion of the outer conductor 326. The cross-sectional dimension of the portion of rigid member 318 extending beyond the distal portion of the outer conductor 326 is substantially similar to the cross-sectional dimension of the feedline 322.

Rigid member 318 defines a lumen 318a formed in at least a portion of the proximal portion "A" and provides support for inner conductor 324 as it transitions from the center of the feedline 322 to the helical portion of the antenna 312b. A cross-sectional dimension of lumen 318a may conform to the dimensions of inner conductor 324 contained therewithin or lumen 318a may be slotted and may slidably engage inner conductor 324. The lumen 318a of rigid member 318 disposed within the feedline 322 may be substantially centered within rigid member 318. In the proximal portion "A" of antenna portion 312b, helical antenna member 316b transitions from the center of the feedline 322 to an outer surface 318b of rigid member 318. Lumen 318a of rigid member 318 supports helical antenna member 316a during the transition from the center of feedline 322 to the outer surface 318b of rigid member 318.

The cross-sectional dimension of the portion of the rigid member 318, disposed within the outer conductor 326, is substantially equal to the cross-sectional dimension of the inner diameter of the outer conductor 326. Rigid member 318 and outer conductor 326 engage and form connection therebetween. Various methods of engagement may be used to secure rigid member 318 within outer conductor 326 such as, for example, a press fit engagement, a threaded engagement, locking tab engagement, a taper lock engagement, chemical engagement, e.g., adhesive or epoxy, or any other suitable engagement method or means.

As illustrated in FIGS. 7A-7G, helical antenna assembly 300b of FIG. 6B may be obtained by adding a structurally rigid member to the helical antenna assembly 300a of FIG. 6A. Helical antenna assembly 300b of FIG. 6B includes a first assembly 440, including a modified feedline 322 and formed by the method illustrated in FIGS. 7A-7C, and a second assembly 441, including an inner conductor 324, a helical antenna member 316b, and rigid member 318.

As illustrated in FIGS. 7A-7C and 7G, first assembly 440 is formed by taking a feedline/coaxial cable 422 of sufficient length and removing inner conductor 424 therefrom to expose coaxial cable 422a with only the outer conductor 426 and insulation 425 (Step 450). Next, a portion of the insulation 425 from the distal portion of the coaxial cable 422b is removed (Step 451).

As illustrated in FIGS. 7C-7F and the flowchart of FIG. 7G, the second assembly 441 is formed by joining helical antenna member 416 and rigid member 418 (Step 452). Helical antenna member 416 may be formed from a portion of any suitable elongated conductive member as discussed hereinabove. At least a portion of helical antenna member 416 is placed within the lumen 418a of rigid member 418. A suitable length of helical antenna member 416 extends distally from the distal end of rigid member 418.

In the formation of the second assembly 441, helical antenna member 416 may be tightly wound around rigid member 418 such that helical antenna member 416 is compressed onto rigid member 418. Alternatively, helical antenna member 416 may be compressed on rigid member 418 such that two or more adjacent windings of helical antenna member 416 contact one another, as discussed hereinabove. Rigid member 418 may contain grooves in which helical antenna member 416 is contained. Alternatively, the helical antenna member 416 may be formed by depositing metal onto the rigid member 418 and the feedline 422 may connect to the helix in any suitable manner, e.g., solder, crimp adhesive, etc.

The cross-sectional area and dimension, along the length of helical antenna member 416, as discussed hereinabove, need not be uniform. For example, the cross-section of the helical portion of helical antenna member 417 may have one or more sides that are substantially flat or may have a transverse cross-sectional dimension of any suitable shape, such as, for example, circular, rectangular, square or oblong.

As illustrated by opposing arrows 453 in FIG. 6B and by step 453 of flowchart of FIG. 7G, the structurally rigid helical antenna is formed by joining the first assembly 440 and the second assembly 441. The joining of first assembly 440 and second assembly 441 is performed by inserting the proximal portion of second assembly 441 into the distal portion of first assembly 440, wherein the distal portion of helical antenna member 316b forms the inner conductor 324 of the feedline 322. At least a portion of rigid member 318 of second assembly 441 may be disposed within at least a portion of first assembly 440 in that region where the insulation 325 has been removed.

With continued reference to FIG. 6B, a distal portion of the outer conductor 326 of the first assembly 440 engages a proximal portion of rigid member 318 of the second assembly 441. Various methods of engagement may be used to secure the rigid member 418 within outer conductor 326, such as, for example, a press fit engagement, a threaded engagement, locking tab engagement, a taper lock engagement, chemical engagement, e.g., adhesive or epoxy, or any other suitable engagement method or means.

Figure 8A:
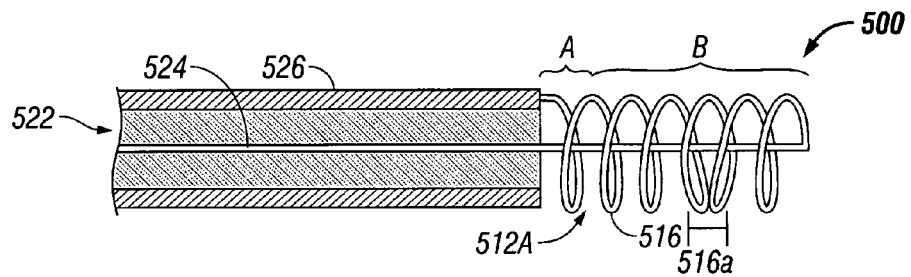
FIG. 8A is a schematic cross-sectional side view of the distal end of a helical microwave antenna assembly including the helical shaped geometry of FIG. 4C.
Figure 8B:
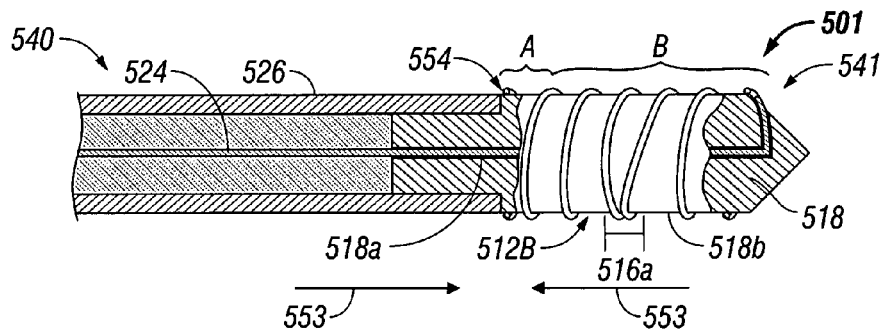
FIG. 8B is a schematic cross-sectional side view of the distal end of the helical microwave antenna assembly of FIG. 8A, having a reinforced configuration.

FIGS. 8A-8B illustrate the microwave antenna assembly of FIG. 4C with the addition of a rigid member and an electrical connection formed in the loop contact area 516a between at least two loops of the helical microwave antenna 516. In FIG. 8A, the antenna portion 512a includes a proximal portion "A" and a distal portion "B". In the proximal portion "A" helical antenna member 516 connects to a distal portion of outer conductor 526. The distal portion "B" of helical antenna member 516 includes the helical shaped portion of helical antenna member 516 and a portion of the inner conductor 524 that extends distally from the feedline 522 and connects to the distal end of the helical portion of the antenna portion 516.

FIG. 8B illustrates the microwave antenna assembly 500 of FIG. 8A with a rigid member 518 for supporting helical antenna member 516 in the antenna portion 512b. A portion of rigid member 518 is disposed within outer conductor 526 of feedline 522 and a portion of rigid member 518 extends beyond the distal portion of the outer conductor 526. The cross-sectional dimension of the portion of rigid member 518 extending beyond the distal portion of the outer conductor 526 is substantially similar to the cross-sectional area of the feedline 522.

Rigid member 518 defines a lumen 518a, located at the radial center of thereof, and extends through a substantial portion thereof. Lumen 518a of rigid member 518 provides a support pathway for the portion of the inner conductor 524 that extends from the distal end of the feedline 522 to the distal end of helical antenna member 518 of antenna portion 512b. Lumen 518a, at the distal end of rigid member 518, is angled to extend from the radial center of rigid member 518 to a perimeter 518b of rigid member 518.

The cross-sectional dimension of the rigid member 518, disposed within the outer conductor 526, is substantially similar to the inner diameter of the outer conductor 526. Rigid member 518 and outer conductor 526 engage and form a connection therebetween. Various methods of engagement may be used to secure the rigid member 518 within outer conductor 526 such as, for example, a press fit engagement, a threaded engagement, locking tab engagement, a taper lock engagement, chemical engagement, e.g., adhesive or epoxy, or any other suitable engagement method or means.

Figure 9A:
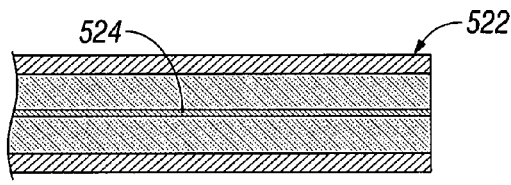
FIGS. 9A-9F illustrate a method of assembling the reinforced helical microwave antenna assembly of FIG. 8B.
Figure 9B:
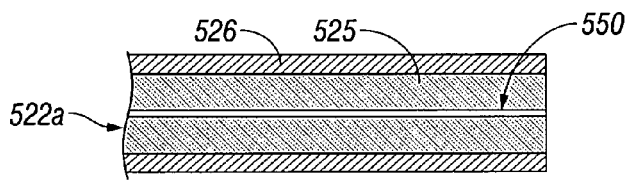
Figure 9C:
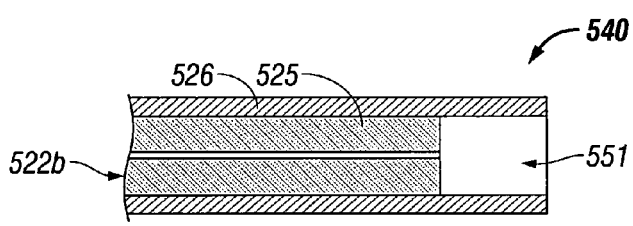
Figure 9D:
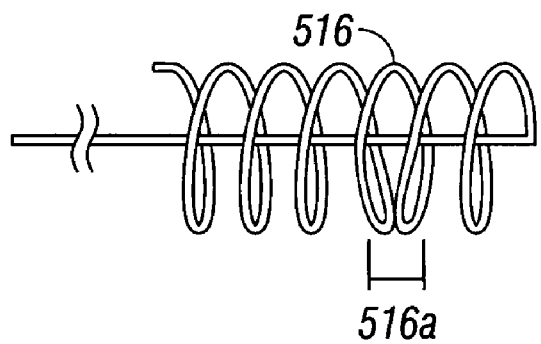
Figure 9E:
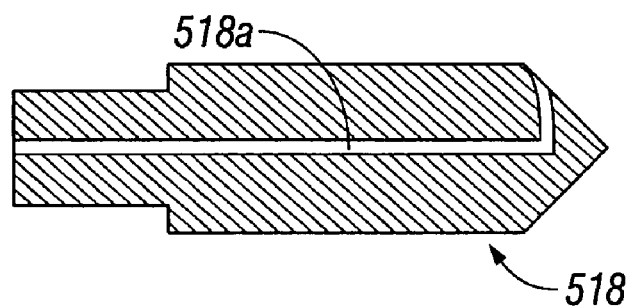
Figure 9F:
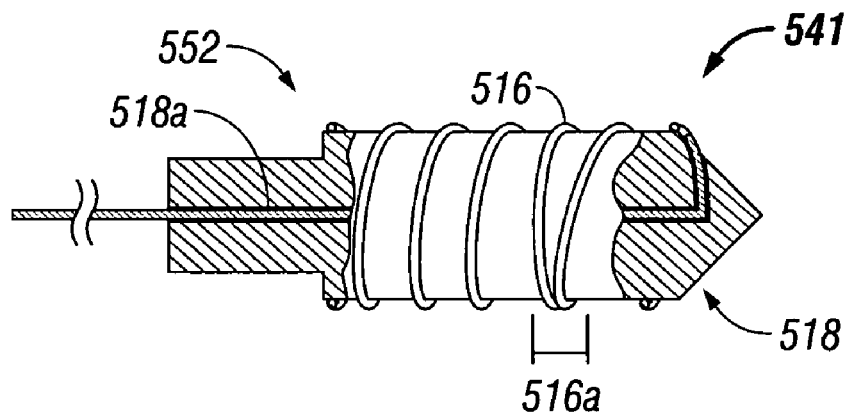
Figure 9G:
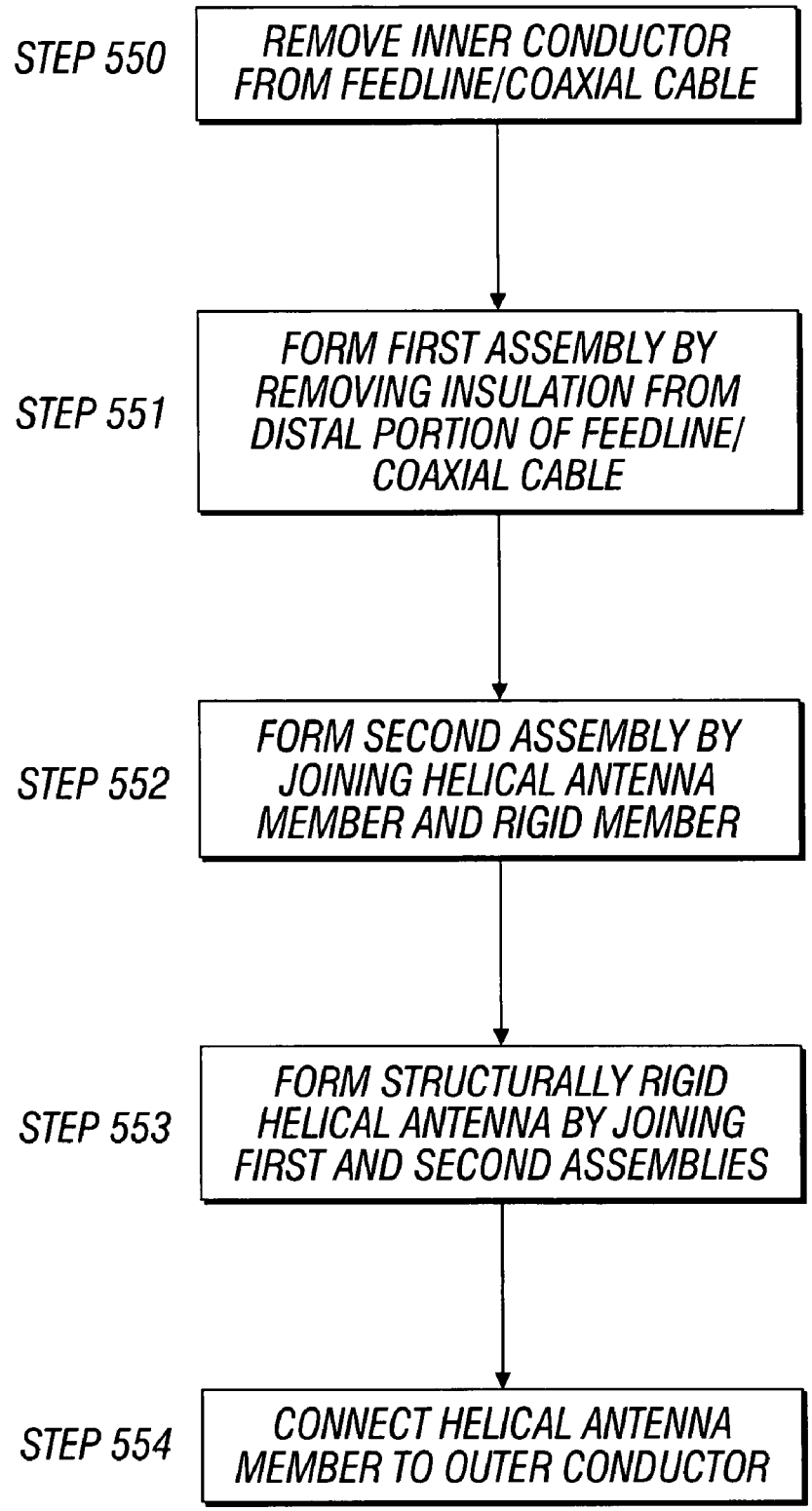
FIG. 9G is a flowchart of the steps in the formation of the structurally rigid helical antenna assembly of FIG. 8B.

Structural rigidity of microwave antenna member 500 (see FIG. 8B), may be obtained by the steps illustrated in FIGS. 9A-9F and the flowchart of FIG. 9G. As seen in FIG. 8B, helical microwave antenna assembly 501 includes a first assembly 540 obtained by the method illustrated in FIGS. 9A-9C and a second assembly 541 obtained by the method illustrated in FIGS. 9D-9F.

As illustrated in FIGS. 9A-9C and the flowchart of FIG. 9G, the first assembly 540 is formed by taking a feedline/coaxial cable 522 of sufficient length and removing the inner conductor 524 to expose the coaxial cable 522a with only the outer conductor 526 and insulation 525 (Step 550). Next, a portion of the insulation 525 from the distal portion of the coaxial cable 522b is removed, (Step 551).

As illustrated in FIGS. 9C-9F and the flowchart of FIG. 9G, the second assembly 541 is formed by joining helical antenna member 516 and rigid member 518 (Step 552). Helical antenna member 516 may be formed from a portion of any suitable elongated conductive member as discussed hereinabove. At least a portion of helical antenna member 516 is placed within the lumen 518a of rigid member 518. A suitable length of helical antenna member 516 extends distally from the distal end of rigid member 518.

The structurally rigid helical antenna is formed by joining the first assembly 540 and second assembly 541 as illustrated by opposing arrows 553 in FIG. 8B and Step 553 of FIG. 9G. The joining of first assembly 540 and second assembly 541 may be performed by inserting the proximal portion of second assembly 541 into the distal portion of first assembly 540. A suitable length of helical antenna member 516 may form the inner conductor 524 of the feedline 522. At least a portion of rigid member 518 of second assembly 541 may be disposed within at least a portion of first assembly 540 in the region where the insulation 525 has been removed.

Next, the proximal end of helical antenna member 516 is connected to the distal portion of the outer conductor 526 (Step 554). Connection may be formed by soldering, welding, crimping or other suitable means of connecting two conductive members.

In accordance with the present disclosure, the contact area 516a may be formed prior to joining the helical antenna member 516 with rigid member. Contact area may be formed while joining or after joining the helical antenna member 516 and rigid member 518. Contact area 16a, 116a, as illustrated in FIGS. 1 and 3, may be formed by positioning, or repositioning one or more loops of the helical antenna 16, 116 to form a contact area 16a, 116a between two or more loops. Loop positioning or loop repositioning may be performed after helical antenna member is disposed on a rigid member thereby creating contact between at least two loops. Alternatively, one or more loops may be compressed and/or deformed thus widening one or more loops thereby creating contact between at least two loops.

The present application discloses cooled helical antennas, various helical antenna geometries, structurally strengthened helical antennas and methods of forming a rigid helical antenna. It is envisioned that the various embodiments described hereinabove may be combined. For example, the methods of forming a rigid helical antenna may be applied to any of the various geometries disclosed and the structurally strengthened helical antennas may be combined and incorporated in the cooled helical microwave antenna assemblies. Modification of the above-described assemblies and methods, and variations of aspects of the disclosure that are obvious to those of skill in the art are intended to be within the scope of the claims.

What is claimed is:

1. A microwave antenna assembly, comprising:
   an elongated cooling jacket having proximal and distal ends and an inner lumen defined therebetween;
   a helical microwave antenna member disposed within at least a portion of the elongated cooling jacket and having an inner and outer conductor, the inner conductor disposed within the outer conductor, wherein at least a portion of the inner conductor extends distally from the outer conductor and forms a plurality of loops;
   wherein at least two loops of the plurality of loops are axially compressed to make electrical contact with one another at a single point to form an electrical connection therebetween, and wherein at least a portion of the plurality of loops is configured to deliver microwave energy.

2. The microwave antenna assembly according to claim 1, further comprising a rigid member that supports the helical microwave antenna, wherein the rigid member engages the distal portion of the outer conductor.

3. The microwave antenna assembly according to claim 2, wherein the rigid member defines a lumen therewithin; and wherein at least a portion of the inner conductor of the helical microwave antenna is disposed within the lumen of the rigid member.

4. The microwave antenna assembly according to claim 3, wherein the at least one loop of the helical microwave antenna member is disposed on the periphery of the rigid member.

5. The microwave antenna assembly according to claim 2, wherein the rigid member comprises a dielectric material.

6. The microwave antenna assembly according to claim 2, wherein a transverse cross-section of a portion of the inner conductor disposed within the outer conductor is different than a transverse cross section of the inner conductor that extends distally from the outer conductor.

7. The microwave antenna assembly according to claim 2, wherein the inner conductor of the helical microwave antenna member further comprises:
   a feedline conductive member; and
   a helical conductive member connected to the distal end of the feedline conductive member;
   wherein a substantial portion of the feedline conductive member is disposed within the outer conductor and a substantial portion of the helical conductive member is distal of the outer conductor.

8. The microwave antenna assembly according to claim 7, wherein a transverse cross-section of the feedline conductive member is different that a transverse cross-section of the helical conductive member.

9. The microwave antenna assembly according to claim 1 further including:
   a sharpened tip adapted to penetrate tissue and attached to the distal end of the elongated cooling jacket and forming a fluid-tight seal; and
   at least one inflow tube that supplies cooling fluid to the distal end of the elongated cooling jacket.

10. The microwave antenna assembly according to claim 9, wherein the elongated cooling jacket further comprises:
    a proximal jacket portion; and
    a distal jacket portion disposed between, and attached to, the proximal jacket portion and the sharpened tip;

wherein a plurality of the at least two loops of the helical microwave antenna member is disposed within the distal jacket portion of the elongated cooling jacket.

11. The microwave antenna assembly according to claim 10, wherein the distal jacket portion comprises a dielectric material.

12. The microwave antenna assembly according to claim 11, further comprising a lubricious coating disposed on an outer surface thereof.

13. The microwave antenna assembly according to claim 11, wherein a proximal jacket portion comprises a conductive material.

14. The microwave antenna assembly according to claim 1, wherein the elongated cooling jacket comprises a dielectric material.

15. A helical microwave antenna, comprising:
a first assembly including:
a tubular outer conductor defining a longitudinal lumen therethrough; and
an insulating member, disposed within at least a portion of the lumen of the outer conductor and defining a longitudinal lumen therewithin; and
a second assembly including:
an elongated conductive member forming a helical loop portion and a feedline portion, the helical loop portion including a plurality of loops, wherein at least two loops of the plurality of loops are axially compressed to make electrical contact with one another at a simile point; and
a rigid member defining a lumen therewithin, the lumen of the rigid member adapted to receive at least a portion of the elongated conductive member, wherein the helical loop portion of the elongated conductive member is disposed on the periphery of a distal portion of the rigid member and at least a portion of the feedline portion extends proximally from the rigid member;
wherein a proximal portion of the second assembly is adapted to engage a distal portion of the first assembly, and wherein at least a portion of the feedline portion of the elongated conductive member is disposed within the lumen of the insulating member.

16. The microwave antenna assembly according to claim 15, wherein the outer conductor of the first assembly engages the rigid member of the second assembly.

17. The microwave antenna assembly according to claim 16, wherein the proximal portion of the second assembly is engaged to the distal portion of the first assembly by at least one of a press fit engagement, a threaded engagement, a taper lock engagement and a chemical engagement.

* * * * *